(12) United States Patent
Meng

(10) Patent No.: US 11,492,343 B2
(45) Date of Patent: Nov. 8, 2022

(54) POLYMORPH OF FLIBANSERIN AND PREPARATION METHOD THEREOF AND USE OF SAME

(71) Applicant: Xiaoming Meng, Tainjin (CN)

(72) Inventor: Xiaoming Meng, Tainjin (CN)

(73) Assignee: Xiaoming Meng, Tianjin (CN)

( * ) Notice: Subject to any disclaimer, the term of this patent is extended or adjusted under 35 U.S.C. 154(b) by 967 days.

(21) Appl. No.: 16/074,130

(22) PCT Filed: Feb. 3, 2017

(86) PCT No.: PCT/CN2017/000143
§ 371 (c)(1),
(2) Date: Jul. 31, 2018

(87) PCT Pub. No.: WO2017/128932
PCT Pub. Date: Aug. 3, 2017

(65) Prior Publication Data
US 2021/0122737 A1    Apr. 29, 2021

(30) Foreign Application Priority Data
Jan. 31, 2016  (CN) .......................... 201610072487.3

(51) Int. Cl.
  *C07D 403/06*   (2006.01)
  *C07D 235/26*   (2006.01)
  *A61K 31/496*   (2006.01)
(52) U.S. Cl.
  CPC ........ *C07D 403/06* (2013.01); *C07B 2200/13* (2013.01)

(58) Field of Classification Search
  CPC ................ C07D 403/06; C07D 235/26; C07B 2200/13; A61K 31/496
  See application file for complete search history.

(56) References Cited

U.S. PATENT DOCUMENTS

2005/0159430 A1\* 7/2005 Bombarda .............. A61P 25/20
                                                       514/254.06
2017/0267634 A1\* 9/2017 Zhang .................. C07D 403/12

FOREIGN PATENT DOCUMENTS

| EP | 0526434 A1 | 2/1993 |
| WO | 03014079 A1 | 2/2003 |
| WO | 03097058 A1 | 11/2003 |
| WO | 2010079045 A2 | 7/2010 |

(Continued)

OTHER PUBLICATIONS

Nowee, S. M., "Antisolvent crystallization: Model identification, experimental validation and dynamic simulation." Chemical Engineering Science 63.22 (2008): 5457-5467.\*

(Continued)

*Primary Examiner* — John M Mauro
(74) *Attorney, Agent, or Firm* — Metis IP LLC

(57) ABSTRACT

The present invention discloses novel polymorphs I, II, and V of a [2-(4-(3-trifluoromethyl-benzyl)piperazin-1-yl) ethyl]-2,3-dihydro-1H-benzimidazol-2-one and a preparation method and application thereof. The polymorph I is a trihydrate crystal, the polymorph II is an anhydrous crystal, and the polymorph V is an anhydrous crystal. When compared with an existing crystal form, the novel polymorphs provides significant advantages in terms of solubility and preparation techniques.

4 Claims, 11 Drawing Sheets

(56) References Cited

FOREIGN PATENT DOCUMENTS

WO        2010146595 A2    12/2010
WO    WO-2017076356 A1  *  5/2017  ........... C07D 235/26

OTHER PUBLICATIONS

WO 2017076356 A1, 2015 effective filing date; WIPO English machine translation; p. 1-71.*
International Search Report in PCT/CN2017/000143 dated May 12, 2017, 9 pages.
Written Opinion in PCT/CN2017/000143 dated May 12, 2017, 9 pages.

* cited by examiner

POLYMORPH OF FLIBANSERIN AND PREPARATION METHOD THEREOF AND USE OF SAME

TECHNICAL FIELD

The present disclosure relates to novel crystals of [2-(4-(3-trifluoromethyl-benzyl)piperazin-1-yl)ethyl]-2,3-dihydro-1H-benzimidazol-2-one and its preparation method and use.

BACKGROUND

Compound 1, Flibanserin, [2-(4-(3-trifluoromethyl-benzyl)piperazin-1-yl)ethyl]-2,3-dihydro-1H-benzimidazol-2-one is a drug approved by the US FDA to reduce serotonin, which inhibits libido, to increase stimulating dopamine levels and to show good efficacy and tolerance to premenopausal women with hypoactive sexual desire disorder (HSDD). Flibanserin has affinity for 5-HT1A and 5-HT2 receptors with the potential application for the treatment of depression, schizophrenia, Parkinson's disease, anxiety, sleep disorders, mental disorders and age-related memory disorders.

Flibanserin has a molecular formula of $C_{20}H_{21}F_3N_4O$ and a molecular weight of 390.40. The chemical structure of flibanserin is as follows:

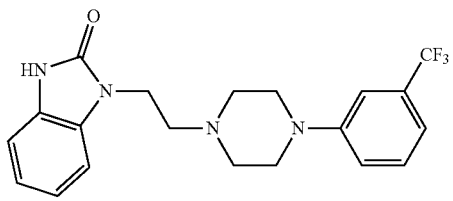 [SMILES: O=c1[nH]c2ccccc2n1CCN1CCN(c2cccc(C(F)(F)F)c2)CC1]

Chemical raw materials of active pharmaceutical ingredients (API) must have good purity, stability, physical and chemical properties and operability. These properties are related to the crystalline form of the drug, and different crystal forms have different physical and chemical properties. The purpose of improving the stability of the drug preservation and the efficacy of the drug, it is necessary to make the raw API into crystal form.

A drug may exist in a plurality of crystalline forms, and different crystal forms of the same drug may have different dissolution and absorption in the body, thereby affecting the dissolution and release of the formulation.

The optimal crystalline form can be discovered by thoroughly studying of the polymorphism of the compound. The optimal crystalline form is crucial to the efficacy of the drug and the formulation process which is based on the characteristics of the crystalline form, thereby effectively ensuring the equivalence of the drug batch to batch.

The found flibanserin crystal forms are described in the following: the hydrochloride salt of flibanserin is reported in European Patent Application EP-A-526,434. The WO2003/014079 patent discloses two crystalline forms of the free base of flibanserin, including the free base Form A and Form B of flibanserin. Form A has a melting point of about 161° C. (determined by DSC, heating rate 10 K/min), and Form B has a melting point of about 120° C. (determined by DSC, heating rate 10K/min). Form B has low stability under pressure and mechanical stress conditions and is not suitable for formulation development. The XRPD pattern of Form A shows that Form A has diffraction peaks at the following 2θ angles: 15.46±0.01, 19.14±0.01, 19.82±0.01, 20.0±0.01, 22.63±0.01, and 24.61±0.01. However, in the prior art, the solubility of flibanserin crystal form A in water is very small, which is disadvantageous to the dissolution and release of the drug, resulting in a decrease in bioavailability and huge variation on drug absorption.

SUMMARY

The main object of the present invention is to provide [2-(4-(3-trifluoromethyl-benzyl)piperazin-1-yl)ethyl]-2,3-dihydro-1H-benzimidazol-2-one (Flibanserin) new crystalline forms, and process for its preparation and a medicinal use.

In this invention, A crystalline form of [2-(4-(3-trifluoromethyl-benzyl)piperazin-1-yl)ethyl]-2,3-dihydro-1H-benzimidazol-2-one designated as Form I, has an X-ray powder diffraction pattern comprising the following 2θ values measured using CuKα radiation: 6.3±0.2, 8.7±0.2, 12.6±0.2, 13.3±0.2, 14.4±0.2, 14.8±0.2, 15.3±0.2, 16.4±0.2, 17.4±0.2, 18.1±0.2, 18.9±0.2, 19.7±0.2, 20.3±0.2, 21.7±0.2, 23.1±0.2, 24.6±0.2, 26.2±0.2, 27.2±0.2 and 27.7±0.2; preferably also including diffraction pattern peaks at 15.8±0.2, 22.3±0.2, 23.6±0.2, 24.2±0.2, 25.0±0.2, 25.4±0.2, 28.1±0.2, 29.5±0.2, 30.9±0.2, 32.9±0.2, 34.6±0.2, 35.1±0.2 and 37.4±0.2.

The melting point of Form I is 76° C. and 161° C. (determined by DSC, at heating rate 10° C./min)

Single crystal data of Form I was collected on a Bruker APEX-II single crystal diffractometer. The single crystal were grew according to the method of Example 33. The collected single crystal data is analyzed to obtain unit cell data as follows:

| | |
|---|---|
| Temperature/K | 293 |
| a/Å | 14.267(2) |
| b/Å | 6.3184(11) |
| c/Å | 24.587(4) |
| α/° | 90 |
| β/° | 101.511(4) |
| γ/° | 90 |
| Volume Å$^3$ | 2171.8(6) |
| Space | P2$_1$/C |
| Z | 4 |
| Calculated density (g/cm$^3$) | 1.359 |
| R factor | 0.0528 |

The structural diagram of single crystal data of crystalline Form I is shown in FIG. 10 which proves that Form I is a trihydrate. The standard X-ray powder diffraction pattern of the crystal Form I is simulated based on the single crystal data. The standard simulated XRPD pattern is shown in FIG. 11, which shows that the simulated diffraction pattern completely coincides with the real-detected XRPD of the crystal form I, indicating that the crystal form I prepared in the experiment does not contain other crystal forms. The single crystal preparation method is as shown in Example 33.

In the present invention, the crystalline Form II of [2-(4-(3-trifluoromethyl-benzyl)piperazin-1-yl)ethyl]-2,3-dihydro-1H-benzimidazol-2-one (Flibanserin), has an X-ray powder diffraction pattern comprising the following 2θ values measured using CuKα radiation: 13.3±0.2, 15.2±0.2, 15.6±0.2, 15.9±0.2, 16.8±0.2, 17.2±0.2, 18.0±0.2, 18.6±0.2, 19.1±0.2, 19.7±0.2, 20.5±0.2, 21.1±0.2, 21.7±0.2, 22.1±0.2, 22.7±0.2, 22.9±0.2, 24.7±0.2, 25.3±0.2 and 28.4±0.2. More diffraction peaks may also be located at 8.3±0.2, 10.4±0.2, 12.6±0.2, 14.0±0.2, 23.5±0.2, 23.9±0.2, 29.1±0.2, 30.4±0.2, 31.9±0.2, 32.6±0.2, 32.9±0.2, 36.3±0.2 and 38.4±0.2. The melting point of Form II is 161° C. (determined by DSC, at heating rate 10° C./min).

[2-(4-(3-trifluoromethyl-benzyl)piperazin-1-yl)ethyl]-2,3-dihydro-1H-benzimidazol-2-one form II is anhydrate.

In the present invention, the crystalline Form V of [2-(4-(3-trifluoromethyl-benzyl)piperazin-1-yl)ethyl]-2,3-dihydro-1H-benzimidazol-2-one (Flibanserin), has an X-ray powder diffraction pattern comprising the following 2θ values measured using CuKα radiation: 11.9±0.2, 13.9±0.2, 14.4±0.2, 14.8±0.2, 17.0±0.2, 17.9±0.2, 19.4±0.2, 21.6.±0.2, 22.7±0.2, 23.0±0.2, 23.5±0.2, 23.9±0.2, and 25.7±0.2 more diffraction peaks may also be located at 5.9±0.2, 9.6±0.2, 11.5±0.2, 15.3±0.2, 20.5±0.2, 25.5±0.2, 26.6±0.2, 27.4±0.2, 28.6±0.2, 29.0±0.2, and 32.1±0.2. The melting point of Form V is 161° C. (determined by DSC, heating rate 10° C./min).

The crystal form V of [2-(4-(3-trifluoromethyl-benzyl)piperazin-1-yl)ethyl]-2,3-dihydro-1H-benzimidazol-2-one is anhydrate.

[2-(4-(3-trifluoromethyl-benzyl)piperazin-1-yl)ethyl]-2,3-dihydro-1H-benzimidazol-2-one Form I, II or V is used as an active ingredient in the pharmaceutical composition.

Method for preparing crystal form I of [2-(4-(3-trifluoromethyl-benzyl)piperazin-1-yl)ethyl]-2,3-dihydro-1H-benzimidazol-2-one is to add sodium carbonate solution into [2-(4-(3-trifluoromethyl-benzyl)piperazin-1-yl)ethyl]-2,3-dihydro-1H-benzimidazol-2-one hydrochloride aqueous solution and collect the solid as Form I after the filtering precipitation.

Method for preparing of crystal form I [2-(4-(3-trifluoromethyl-benzyl)piperazin-1-yl)ethyl]-2,3-dihydro-1H-benzimidazol-2-one is described as following: [2-(4-(3-trifluoromethyl-benzyl)piperazin-1-yl)ethyl]-2,3-dihydro-1H-benzimidazol-2-one is dissolved in a good solvent, then water is added to the solution, and the solid is precipitated and then filtered to obtain Form I.

Method for preparing of crystal form I [2-(4-(3-trifluoromethyl-benzyl)piperazin-1-yl)ethyl]-2,3-dihydro-1H-benzimidazol-2-one is described as following: [2-(4-(3-trifluoromethyl-benzyl)piperazin-1-yl)ethyl]-2,3-dihydro-1H-benzimidazol-2-one is dissolved in a good solvent, then add the solution into water, and the solid is precipitated and then filtered to obtain Form I.

Method for preparing of crystal form I [2-(4-(3-trifluoromethyl-benzyl)piperazin-1-yl)ethyl]-2,3-dihydro-1H-benzimidazol-2-one is described as following: [2-(4-(3-trifluoromethyl-benzyl)piperazin-1-yl)ethyl]-2,3-dihydro-1H-benzimidazol-2-one is dissolved in heated good solvent or water, then cooling down the heated solution to get precipitation as Form I by filtration.

Method for preparing [2-(4-(3-trifluoromethyl-benzyl)piperazin-1-yl)ethyl]-2,3-dihydro-1H-benzimidazol-2-one crystal form II is described as following: Let [2-(4-(3-trifluoromethyl-benzyl)piperazin-1-yl)ethyl]-2,3-dihydro-1H-benzimidazol-2-one crystal form I dry in vacuum and the Form II is obtained.

Method for preparing [2-(4-(3-trifluoromethyl-benzyl)piperazin-1-yl)ethyl]-2,3-dihydro-1H-benzimidazol-2-one crystal form V is described as following: [2-(4-(3-trifluoromethyl-benzyl)piperazin-1-yl)ethyl]-2,3-dihydro-1H-benzimidazol-2-one is dissolved in 2-methyltetrahydrofuran, this solution is added to a poor solvent, and the solid is precipitated and then filtered to obtain Form V.

The beneficial effects of the present invention compared to the prior art are: The solubility and dissolution rate of [2-(4-(3-trifluoromethyl benzyl) piperazin-1-yl)ethyl]-2,3-dihydro-1H-benzimidazol-2-one crystal forms I, II, and V in physiological solution are greater than the existing [2-(4-(3-trifluoromethyl-benzyl)piperazin-1-yl)ethyl]-2,3-dihydro-1H-benzimidazol-2-one crystal form A. Therefore, in terms of solubility, the anhydrate has a distinct advantage over the hydrate.

DETAILED DESCRIPTION

The specific embodiments of the present invention are further described in detail below with reference to the drawings and embodiments. The following examples are intended to illustrate the invention, but are not intended to limit the scope of the invention.

Example 1

1.0 g of [2-(4-(3-trifluoromethyl-benzyl)piperazin-1-yl)ethyl]-2,3-dihydro-1H-benzimidazol-2-one hydrochloride is dissolved in 400 mL of water, and added 2 mg/ml sodium carbonate solution till the solid was precipitated and then filtered the precipitation to obtain [2-(4-(3-trifluoromethyl-benzyl) piperazin-1-yl)ethyl]-2,3-dihydro-1H-benzimidazol-2-one Form I.

The X-ray powder diffraction operation and analysis steps in this patent are as follows:

The Rigaku Ultima IV powder diffractometer was used, which was irradiated with Cu-Kα (40 kV, 40 mA) at room temperature using a D/tex Ultra detector. The scanning range is from 3° to 45° in the 2θ interval, and the scanning speed is 20°/min.

Measurement differences associated with X-ray powder diffraction analysis results are produced by a variety of factors including: (a) errors in sample preparation (eg, sample height), (b) instrument error, (c) calibration differences, (d) operator error (including errors that occur when determining peak position), and (e) properties of the substance (eg, preferred orientation error). Calibration errors and sample height errors often result in displacement of all peaks in the same direction. When using a flat sampler, small differences in sample height will result in large displacements of the XRPD peak position. Systematic studies have shown that a 1 mm sample height difference can result in a 2θ peak shift of up to 1°. These displacements can be identified from the X-ray diffraction pattern and can be eliminated by compensating for the displacement (using a system calibration factor for all peak position values) or recalibrating the instrument. As described above, the measurement errors from different instruments can be corrected by applying a system calibration factor to make the peak positions consistent.

Figure 1:
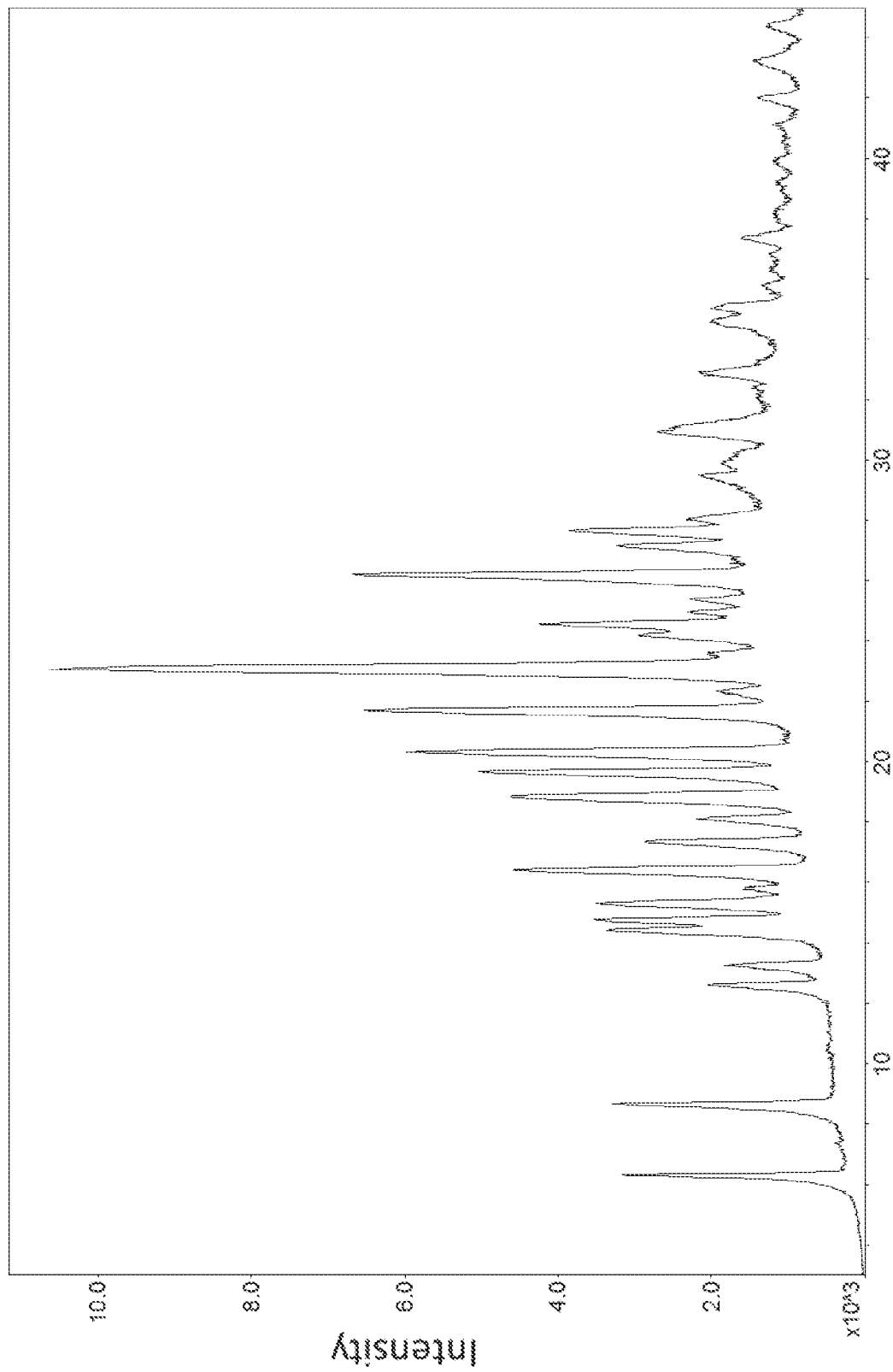
FIG. 1 XPRD pattern of [2-(4-(3-trifluoromethyl-benzyl)piperazin-1-yl)ethyl]-2,3-dihydro-1H-benzimidazol-2-one Form I.

[2-(4-(3-trifluoromethyl-benzyl)piperazin-1-yl)ethyl]-2,3-dihydro-1H-benzimidazol-2-one designated as Form I, has an X-ray powder diffraction pattern comprising the following 2θ values measured using CuKα radiation: 6.3±0.2, 8.7±0.2, 12.6±0.2, 13.3±0.2, 14.4±0.2, 14.8±0.2, 15.3±0.2, 15.8±0.2, 16.4±0.2 17.4±0.2, 18.1±0.2, 18.9±0.2, 19.7±0.2, 20.3±0.2, 21.7±0.2, 22.3±0.2, 23.1±0.2, 23.6±0.2, 24.2±0.2, 24.6±0.2, 25.0±0.2, 25.4±0.2, 26.2±0.2, 27.2±0.2, 27.7±0.2, 28.1±0.2, 29.5±0.2, 30.9±0.2, 32.9±0.2, 34.6±0.2, 35.1±0.2 and 37.4±0.2. The XRPD patterns is shown in FIG. 1 and the diffraction peaks of the XRPD pattern of Form I are listed in the following table:

| 2-Theta | d(A) | I(Height)% |
|---|---|---|
| 6.339 | 13.9316 | 32.1 |
| 8.698 | 10.1574 | 31.7 |
| 12.639 | 6.9978 | 16.6 |
| 13.281 | 6.6612 | 13.1 |
| 14.44 | 6.1289 | 30.4 |
| 14.816 | 5.9741 | 26.1 |
| 15.339 | 5.7719 | 25 |
| 15.804 | 5.603 | 6.1 |
| 16.42 | 5.3939 | 39.2 |
| 17.361 | 5.1038 | 22.3 |
| 18.12 | 4.8917 | 13.2 |
| 18.86 | 4.7014 | 37.8 |
| 19.699 | 4.503 | 42.3 |
| 20.34 | 4.3625 | 52.2 |
| 21.72 | 4.0883 | 57.3 |
| 22.34 | 3.9763 | 6 |
| 23.061 | 3.8535 | 100 |
| 23.637 | 3.7609 | 5.8 |
| 24.2 | 3.6747 | 15 |
| 24.579 | 3.6188 | 29.3 |
| 24.961 | 3.5644 | 7 |
| 25.399 | 3.5038 | 6.8 |
| 26.219 | 3.396 | 55.1 |
| 27.178 | 3.2784 | 16.3 |
| 27.679 | 3.2202 | 25.1 |
| 28.059 | 3.1774 | 6.8 |
| 29.518 | 3.0236 | 8.4 |
| 29.92 | 2.9839 | 4.8 |
| 30.94 | 2.8878 | 14.8 |
| 32.938 | 2.7171 | 9.7 |
| 34.581 | 2.5917 | 9.5 |
| 35.078 | 2.556 | 8.3 |
| 35.799 | 2.5062 | 2.6 |
| 36.267 | 2.475 | 1.6 |
| 36.84 | 2.4378 | 2.2 |
| 37.361 | 2.4049 | 6 |
| 39.274 | 2.2921 | 2 |
| 39.921 | 2.2564 | 2.2 |
| 41.124 | 2.1932 | 2.8 |
| 42.038 | 2.1476 | 5.5 |
| 43.259 | 2.0897 | 6.4 |
| 44.381 | 2.0395 | 4.6 |

A differential scanning calorimetry (DSC) analysis was performed on the crystal form I in Example 1, using a TA Q2000 differential scanning calorimeter using an N2 atmosphere at a temperature rising rate of 10° C./min.

Figure 4:
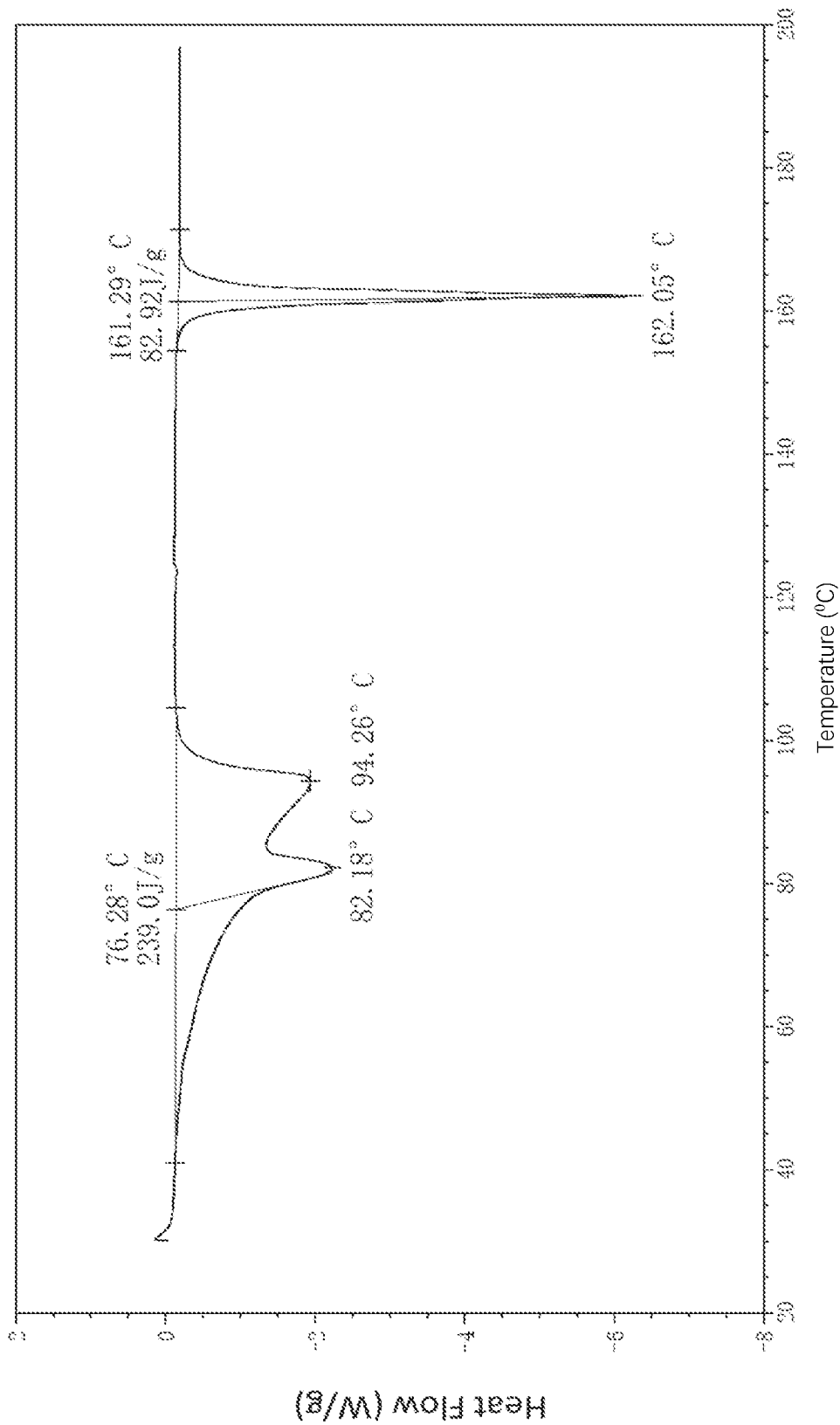
FIG. 4 DSC plot of [2-(4-(3-trifluoromethyl-benzyl)piperazin-1-yl)ethyl]-2,3-dihydro-1H-benzimidazol-2-one Form I.

The DSC plot of Form I is shown in FIG. 4, in which the first stage is the dehydration process and the second stage is the melting process after the water loss.

The thermogravimetric (TGA) analysis of the crystal form I in Example 1 was carried out using a TA Q500 thermogravimetric analyzer using a $N_2$ atmosphere at a heating rate of 10° C./min.

Figure 7:
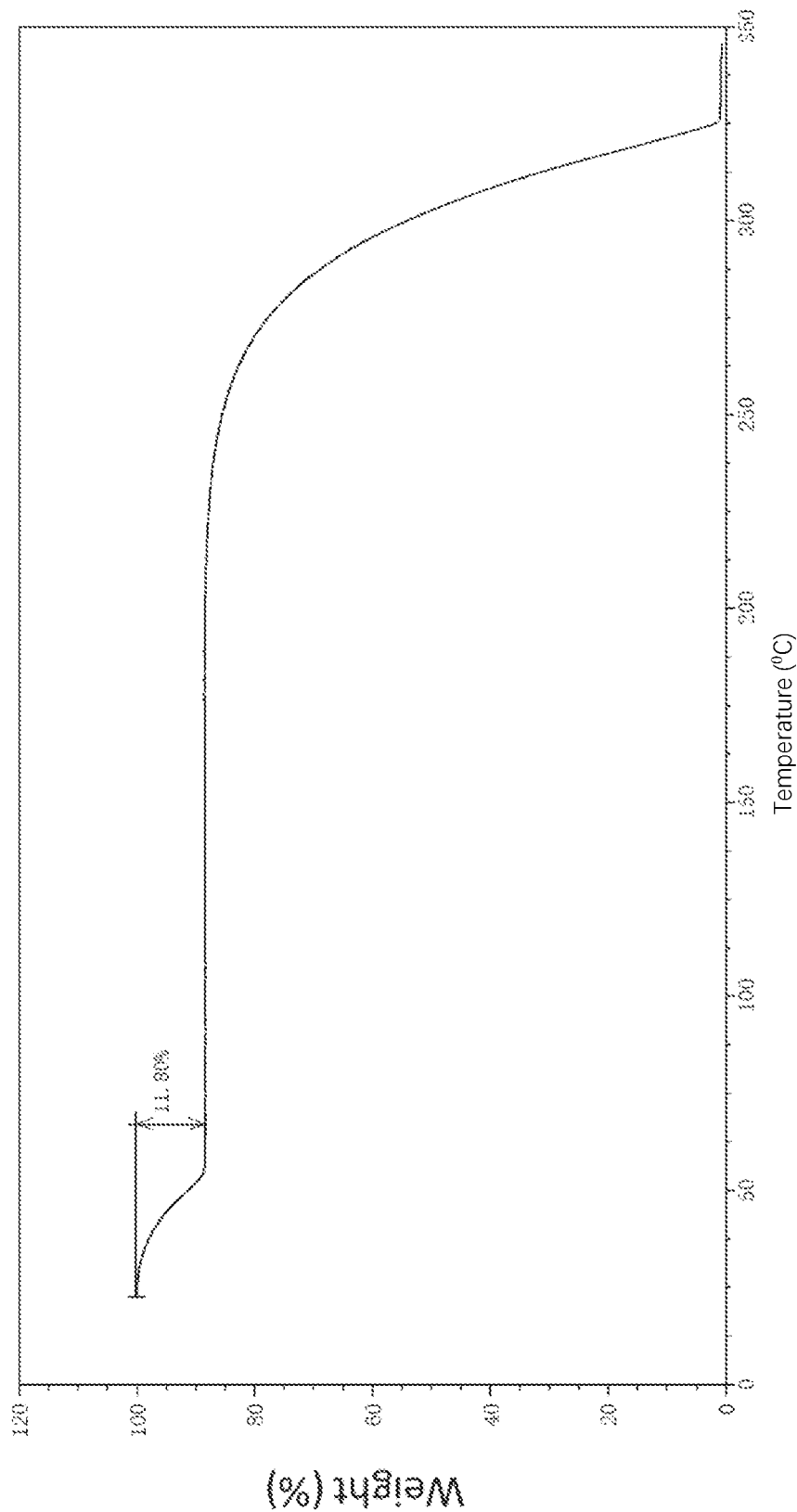
FIG. 7 TGA plot of [2-(4-(3-trifluoromethyl-benzyl)piperazin-1-yl)ethyl]-2,3-dihydro-1H-benzimidazol-2-one Form I.

The TGA plot of Form I is shown in FIG. 7. The weight loss of 11.8% before 60° C. is the heating and dehydration process.

Example 2

20 mg of [2-(4-(3-trifluoromethyl-benzyl)piperazin-1-yl)ethyl]-2,3-dihydro-1H-benzimidazol-2-one was dissolved in 0.5 mL ethanol, 2 ml of water was added thereto, and the solid was precipitated and filtered to give [2-(4-(3-trifluoromethyl-benzyl)piperazin-1-yl)ethyl]-2,3-dihydro-1H-benzimidazol-2-one Form I.

Example 3

20 mg of [2-(4-(3-trifluoromethyl-benzyl)piperazin-1-yl)ethyl]-2,3-dihydro-1H-benzimidazol-2-one was dissolved in 1 mL n-propanol, 2 ml of water was added thereto, and the solid was precipitated and filtered to give [2-(4-(3-trifluoromethyl-benzyl)piperazin-1-yl)ethyl]-2,3-dihydro-1H benzimidazol-2-one Form I.

Example 4

20 mg of [2-(4-(3-trifluoromethyl-benzyl)piperazin-1-yl)ethyl]-2,3-dihydro-1H-benzimidazol-2-one was dissolved in 1 mL isopropanol, 4 ml of water was added thereto, and the solid was precipitated and filtered to give [2-(4-(3-trifluoromethyl-benzyl)piperazin-1-yl)ethyl]-2,3-dihydro-1H-benzimidazol-2-one Form I.

Example 5

20 mg of [2-(4-(3-trifluoromethyl-benzyl)piperazin-1-yl)ethyl]-2,3-dihydro-1H-benzimidazol-2-one was dissolved in 1 mL acetonitrile, 4 ml of water was added thereto, and the solid was precipitated and filtered to give [2-(4-(3-trifluoromethyl-benzyl)piperazin-1-yl)ethyl]-2,3-dihydro-1H-benzimidazol-2-one Form I.

Example 6

50 mg of [2-(4-(3-trifluoromethyl-benzyl)piperazin-1-yl)ethyl]-2,3-dihydro-1H-benzimidazol-2-one was dissolved in 1 mL methanol, 4 ml of water was added thereto, and the solid was precipitated and filtered to give [2-(4-(3-trifluoromethyl-benzyl)piperazin-1-yl)ethyl]-2,3-dihydro-1H-benzimidazol-2-one Form I.

Example 7

50 mg of [2-(4-(3-trifluoromethyl-benzyl)piperazin-1-yl)ethyl]-2,3-dihydro-1H-benzimidazol-2-one was dissolved in 1 mL trifluoroethanol, 4 ml of water was added thereto, and the solid was precipitated and filtered to give [2-(4-(3-trifluoromethyl-benzyl)piperazin-1-yl)ethyl]-2,3-dihydro-1H-benzimidazol-2-one Form I.

Example 8

50 mg of [2-(4-(3-trifluoromethyl-benzyl)piperazin-1-yl)ethyl]-2,3-dihydro-1H-benzimidazol-2-one was dissolved in 1 mL acetone, 4 ml of water was added thereto, and the solid was precipitated and filtered to give [2-(4-(3-trifluoromethyl-benzyl)piperazin-1-yl)ethyl]-2,3-dihydro-1H-benzimidazol-2-one Form I.

Example 9

50 mg of [2-(4-(3-trifluoromethyl-benzyl)piperazin-1-yl)ethyl]-2,3-dihydro-1H-benzimidazol-2-one was dissolved in 1 mL ethylene glycol dimethyl ether, 4 ml of water was added thereto, and the solid was precipitated and filtered to give [2-(4-(3-trifluoromethyl-benzyl)piperazin-1-yl)ethyl]-2,3-dihydro-1H-benzimidazol-2-one Form I.

Example 10

100 mg of [2-(4-(3-trifluoromethyl-benzyl)piperazin-1-yl)ethyl]-2,3-dihyrdo-1H-benzimidazol-2-one was dissolved in 1 mL N,N-dimethylformamide, 4 ml of water was added thereto, and the solid was precipitated and filtered to give [2-(4-(3-trifluoromethyl-benzyl)piperazin-1-yl)ethyl]-2,3-dihydro-1H-benzimidazol-2-one Form I.

Example 11

100 mg of [2-(4-(3-trifluoromethyl-benzyl)piperazin-1-yl)ethyl]-2,3-dihydro-1H-benzimidazol-2-one was dissolved in 1 mL, 4-dioxane, 4 ml of water was added thereto, and the solid was precipitated and filtered to give [2-(4-(3-trifluoromethyl-benzyl)piperazin-1-yl)ethyl]-2,3-dihydro-1H-benzimidazol-2-one Form I.

Example 12

100 mg of [2-(4-(3-trifluoromethyl-benzyl)piperazin-1-yl)ethyl]-2,3-dihydro-1H-benzimidazol-2-one was dissolved in 1 mL tetrahydrofuran, 4 ml of water was added thereto, and the solid was precipitated and filtered to give [2-(4-(3-trifluoromethyl-benzyl)piperazin-1-yl)ethyl]-2,3-dihydro-1H-benzimidazol-2-one Form I.

Example 13

100 mg of [2-(4-(3-trifluoromethyl-benzyl)piperazin-1-yl)ethyl]-2,3-dihydro-1H-benzimidazol-2-one was dissolved in 1 mL pyridine, 4 ml of water was added thereto, and the solid was precipitated and filtered to give [2-(4-(3-trifluoromethyl-benzyl)piperazin-1-yl)ethyl]-2,3-dihydro-1H-benzimidazol-2-one Form I.

Example 14

20 mg of [2-(4-(3-trifluoromethyl-benzyl)piperazin-1-yl)ethyl]-2,3-dihydro-1H-benzimidazol-2-one was dissolved in 0.5 ml ethanol, this solution was added dropwise to 2 ml of 4° C. water, and the solid was precipitated and filtered to give [2-(4-(3-trifluoromethyl-benzyl)piperazin-1-yl)ethyl]-2,3-dihydro-1H-benzimidazol-2-one Form I.

Example 15

20 mg of [2-(4-(3-trifluoromethyl-benzyl)piperazin-1-yl)ethyl]-2,3-dihydro-1H-benzimidazol-2-one was dissolved in 0.5 ml n-propanol, this solution was added dropwise to 2 ml of 4° C. water, and the solid was precipitated and filtered to give [2-(4-(3-trifluoromethyl-benzyl)piperazin-1-yl)ethyl]-2,3-dihydro-1H-benzimidazol-2-one Form I.

Example 16

20 mg of [2-(4-(3-trifluoromethyl-benzyl)piperazin-1-yl)ethyl]-2,3-dihydro-1H-benzimidazol-2-one was dissolved in 1 ml isopanol, this solution was added dropwise to 4 ml of 4° C. water, and the solid was precipitated and filtered to give [2-(4-(3-trifluoromethyl-benzyl)piperazin-1-yl)ethyl]-2,3-dihydro-1H-benzimidazol-2-one Form I.

Example 17

20 mg of [2-(4-(3-trifluoromethyl-benzyl)piperazin-1-yl)ethyl]-2,3-dihydro-1H-benzimidazol-2-one was dissolved in 1 ml acetonitrile, this solution was added dropwise to 4 ml of 4° C. water, and the solid was precipitated and filtered to give [2-(4-(3-trifluoromethyl-benzyl)piperazin-1-yl)ethyl]-2,3-dihydro-1H-benzimidazol-2-one Form I.

Example 18

50 mg of [2-(4-(3-trifluoromethyl-benzyl)piperazin-1-yl)ethyl]-2,3-dihydro-1H-benzimidazol-2-one was dissolved in 0.5 ml methanol, this solution was added dropwise to 2 ml of 4° C. water, and the solid was precipitated and filtered to give [2-(4-(3-trifluoromethyl-benzyl)piperazin-1-yl)ethyl]-2,3-dihydro-1H-benzimidazol-2-one Form I.

Example 19

50 mg of [2-(4-(3-trifluoromethyl-benzyl)piperazin-1-yl)ethyl]-2,3-dihydro-1H-benzimidazol-2-one was dissolved in 1 ml trifluoroethanol, this solution was added dropwise to 4 ml of 4° C. water, and the solid was precipitated and filtered to give [2-(4-(3-trifluoromethyl-benzyl)piperazin-1-yl)ethyl]-2,3-dihydro-1H-benzimidazol-2-one Form I.

Example 20

50 mg of [2-(4-(3-trifluoromethyl-benzyl)piperazin-1-yl)ethyl]-2,3-dihydro-1H-benzimidazol-2-one was dissolved in 1 ml acetone, this solution was added dropwise to 4 ml of 4° C. water, and the solid was precipitated and filtered to give [2-(4-(3-trifluoromethyl-benzyl)piperazin-1-yl)ethyl]-2,3-dihydro-1H-benzimidazol-2-one Form I.

Example 21

50 mg of [2-(4-(3-trifluoromethyl-benzyl)piperazin-1-yl)ethyl]-2,3-dihydro-1H-benzimidazol-2-one was dissolved in 1 ml ethylene glycol dimethyl ether, this solution was added dropwise to 4 ml of 4° C. water, and the solid was precipitated and filtered to give [2-(4-(3-trifluoromethyl-benzyl)piperazin-1-yl)ethyl]-2,3-dihydro-1H-benzimidazol-2-one Form I.

Example 22

100 mg of [2-(4-(3-trifluoromethyl-benzyl)piperazin-1-yl)ethyl]-2,3-dihydro-1H-benzimidazol-2-one was dissolved in 1 ml N,N-dimethylformamide, this solution was added dropwise to 4 ml of 4° C. water, and the solid was precipitated and filtered to give [2-(4-(3-trifluoromethyl-benzyl)piperazin-1-yl)ethyl]-2,3-dihydro-1H-benzimidazol-2-one Form I.

Example 23

100 mg of [2-(4-(3-trifluoromethyl-benzyl)piperazin-1-yl)ethyl]-2,3-dihydro-1H-benzimidazol-2-one was dissolved in 1 ml 1,4-dioxane, this solution was added dropwise to 4 ml of 4° C. water, and the solid was precipitated and filtered to give [2-(4-(3-trifluoromethyl-benzyl)piperazin-1-yl)ethyl]-2,3-dihydro-1H-benzimidazol-2-one Form I.

Example 24

100 mg of [2-(4-(3-trifluoromethyl-benzyl)piperazin-1-yl)ethyl]-2,3-dihydro-1H-benzimidazol-2-one was dissolved in 1 ml tetrahydrofuran, this solution was added dropwise to 4 ml of 4° C. water, and the solid was precipitated and filtered to give [2-(4-(3-trifluoromethyl-benzyl)piperazin-1-yl)ethyl]-2,3-dihydro-1H-benzimidazol-2-one Form I.

Example 25

100 mg of [2-(4-(3-trifluoromethyl-benzyl)piperazin-1-yl)ethyl]-2,3-dihydro-1H-benzimidazol-2-one was dissolved in 1 ml pyridine, this solution was added dropwise to 4 ml of 4° C. water, and the solid was precipitated and filtered to give [2-(4-(3-trifluoromethyl-benzyl)piperazin-1-yl)ethyl]-2,3-dihydro-1H-benzimidazol-2-one Form I.

Example 26

20 mg of [2-(4-(3-trifluoromethyl-benzyl)piperazin-1-yl)ethyl]-2,3-dihydro-1H-benzimidazol-2-one was dissolved in 1 ml 50° C. ethanol/water (2:1, v/v), this solution was cooled to 0° C., and the solid was precipitated and filtered to give [2-(4-(3-trifluoromethyl-benzyl)piperazin-1-yl)ethyl]-2,3-dihydro-1H-benzimidazol-2-one-one Form I.

Example 27

20 mg of [2-(4-(3-trifluoromethyl-benzyl)piperazin-1-yl)ethyl]-2,3-dihydro-1H-benzimidazol-2-one was dissolved in 1 ml 50° C. n-propanol/water (2:1, v/v), this solution was cooled to 0° C., and the solid was precipitated and filtered to give [2-(4-(3-trifluoromethyl-benzyl)piperazin-1-yl)ethyl]-2,3-dihydro-1H-benzimidazol-2-one Form I.

Example 28

20 mg of [2-(4-(3-trifluoromethyl-benzyl)piperazin-1-yl)ethyl]-2,3-dihydro-1H-benzimidazol-2-one was dissolved in 1 ml 50° C. isopanol/water (2:1, v/v), this solution was cooled to 0° C., and the solid was precipitated and filtered to give [2-(4-(3-trifluoromethyl-benzyl)piperazin-1-yl)ethyl]-2,3-dihydro-1H-benzimidazol-2-one Form I.

Example 29

20 mg of [2-(4-(3-trifluoromethyl-benzyl)piperazin-1-yl)ethyl]-2,3-dihydro-1H-benzimidazol-2-one was dissolved in 1 ml 50° C. acetonitrilel/water (2:1, v/v), this solution was cooled to 0° C., and the solid was precipitated and filtered to give [2-(4-(3-trifluoromethyl-benzyl)piperazin-1-yl)ethyl]-2,3-dihydro-1H-benzimidazol-2-one Form I.

Example 30

[2-(4-(3-trifluoromethyl-benzyl)piperazin-1-yl)ethyl]-2,3-dihydro-1H-benzimidazol-2-one form I prepared in Example 1 crystal was dried under vacuum at room temperature to give [2-(4-(3-trifluoromethyl-benzyl)piperazin-1-yl)ethyl]-2,3-dihydro-1H-benzimidazol-2-one crystal form II.

Figure 2:
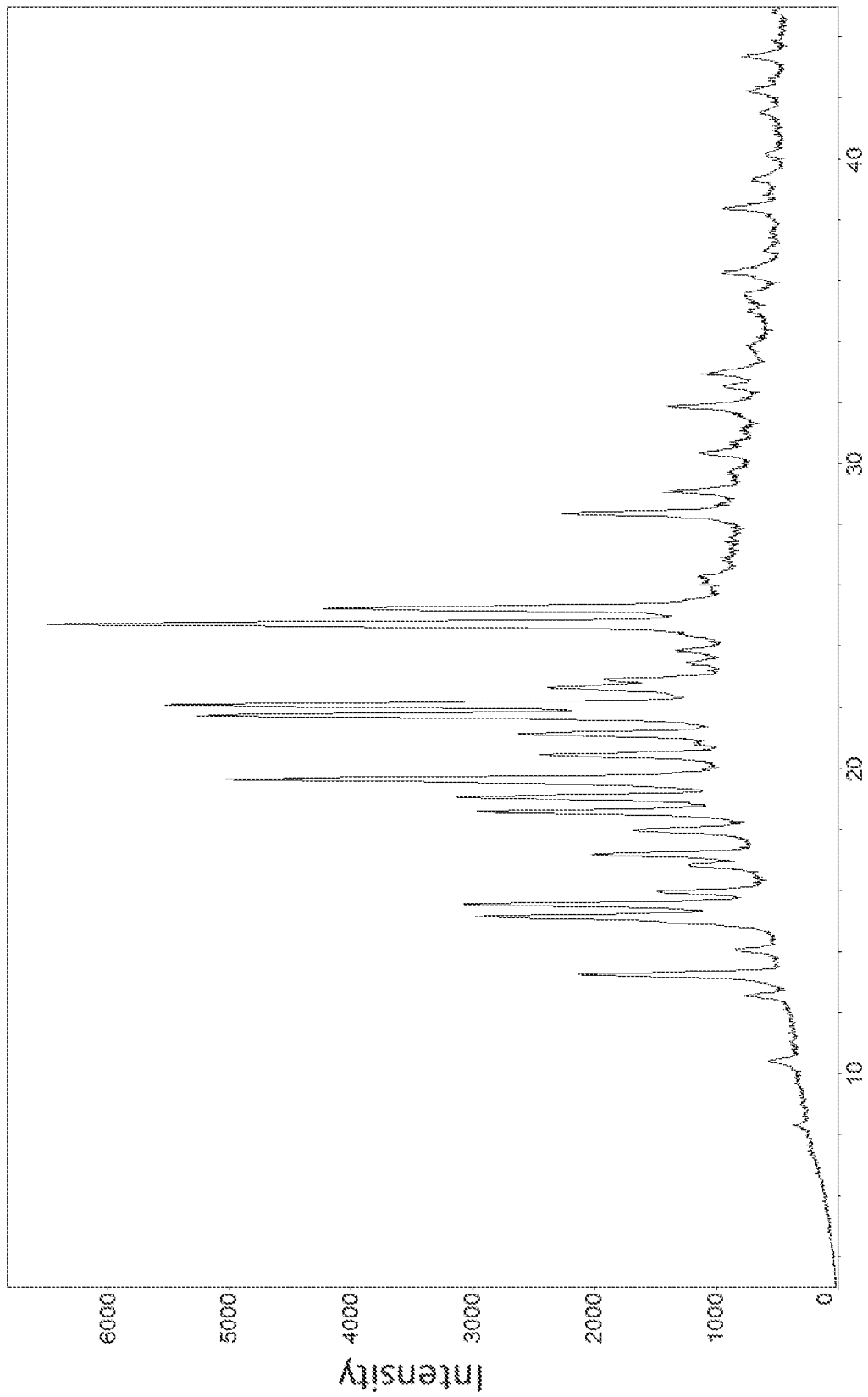
FIG. 2 XPRD pattern of [2-(4-(3-trifluoromethyl-benzyl)piperazin-1-yl)ethyl]-2,3-dihydro-1H-benzimidazol-2-one Form II.

[2-(4-(3-trifluoromethyl-benzyl)piperazin-1-yl)ethyl]-2,3-dihydro-1H-benzimidazol-2-one designated as Form II, has an X-ray powder diffraction pattern comprising the following 2θ values measured using CuKα radiation: 8.3±0.2, 10.4±0.2, 12.6±0.2, 13.3±0.2, 14.0±0.2, 15.2±0.2, 15.6±0.2, 15.9±0.2, 16.8±0.2 17.2±0.2, 18.0±0.2, 18.6±0.2, 19.1±0.2, 19.7±0.2, 20.5±0.2, 21.1±0.2, 21.7±0.2, 22.1±0.2, 22.7±0.2, 22.9±0.2, 23.5±0.2, 23.9±0.2, 24.7±0.2, 25.3±0.2, 28.4±0.2, 29.1±0.2, 30.4±0.2, 31.9±0.2, 32.6±0.2, 32.9±0.2, 36.3±0.2, and 38.4±0.2. The XRPD patterns is shown in FIG. 2 and the diffraction peaks of the XRPD pattern of Form II are listed in the following table:

| 2-Theta | d(A) | I(Height)% |
|---|---|---|
| 8.337 | 10.5971 | 2.1 |
| 10.402 | 8.497 | 4.6 |
| 12.561 | 7.0412 | 5.6 |
| 13.259 | 6.6718 | 29.6 |
| 14.045 | 6.3004 | 5.3 |
| 15.16 | 5.8395 | 43.1 |
| 15.559 | 5.6907 | 44.9 |
| 15.981 | 5.5413 | 12.5 |
| 16.822 | 5.2661 | 9.8 |
| 17.199 | 5.1513 | 23.9 |
| 17.999 | 4.9243 | 16 |
| 18.599 | 4.7668 | 34.2 |
| 19.097 | 4.6435 | 40.2 |
| 19.659 | 4.512 | 72.1 |
| 20.477 | 4.3337 | 25.6 |
| 21.141 | 4.199 | 27.7 |
| 21.741 | 4.0845 | 73.7 |
| 22.081 | 4.0223 | 80.4 |
| 22.661 | 3.9207 | 21.2 |
| 22.92 | 3.8768 | 14.3 |
| 23.495 | 3.7833 | 4.3 |
| 23.878 | 3.7235 | 5.9 |
| 24.74 | 3.5957 | 100 |
| 25.261 | 3.5227 | 58.4 |
| 28.362 | 3.1442 | 26.1 |
| 29.082 | 3.0679 | 10.2 |
| 30.36 | 2.9416 | 7.1 |
| 31.879 | 2.8049 | 12.7 |
| 32.557 | 2.748 | 4.5 |
| 32.942 | 2.7168 | 8.4 |
| 35 | 2.5616 | 3.2 |
| 35.542 | 2.5237 | 3.7 |
| 36.26 | 2.4754 | 7.3 |
| 38.382 | 2.3433 | 7.7 |
| 39.286 | 2.2914 | 3.3 |
| 40.18 | 2.2425 | 1.7 |
| 41.541 | 2.1721 | 2.3 |
| 42.22 | 2.1387 | 5 |
| 43.342 | 2.0859 | 6 |

Figure 5:
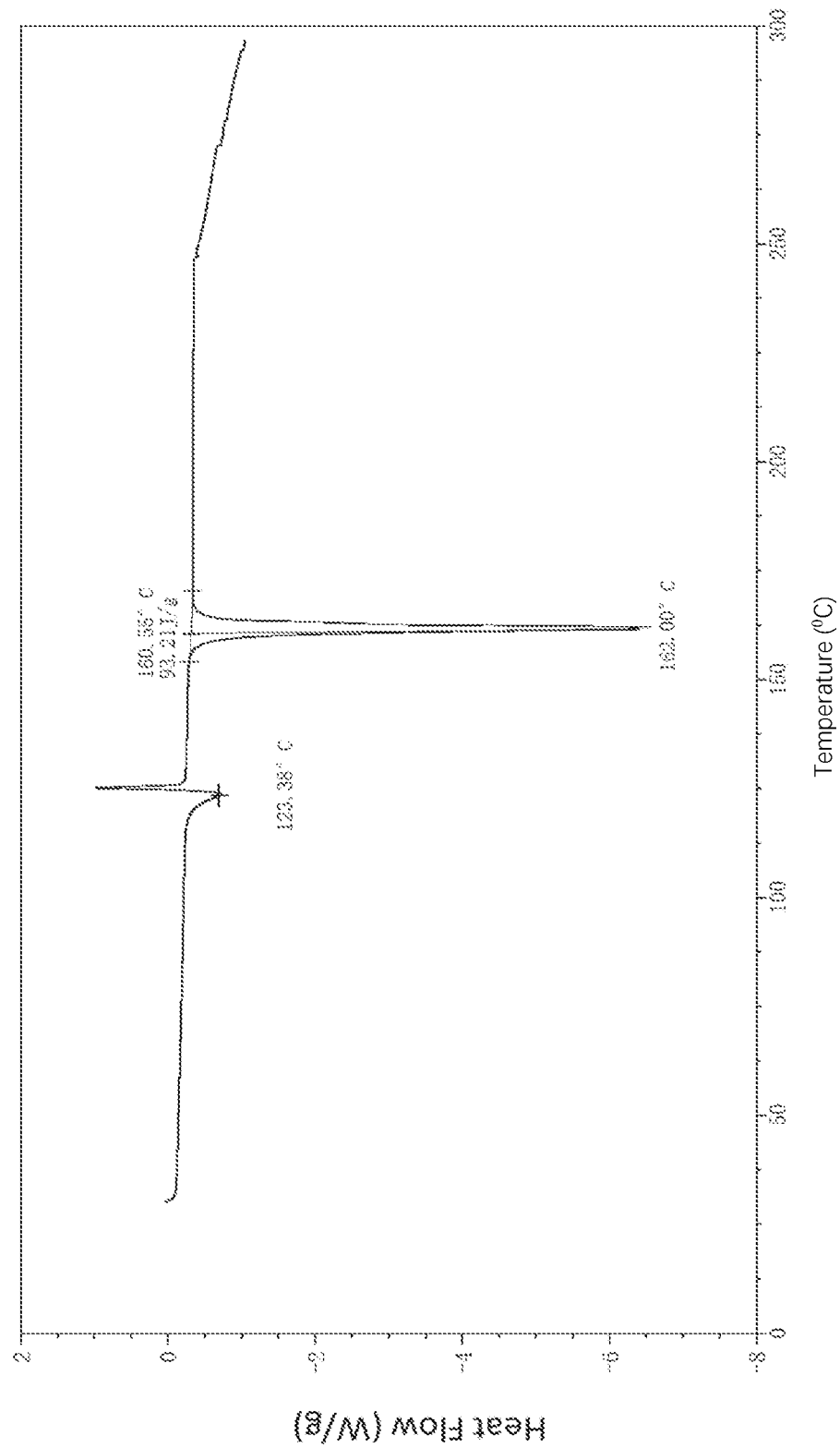
FIG. 5 DSC plot of [2-(4-(3-trifluoromethyl-benzyl)piperazin-1-yl)ethyl]-2,3-dihydro-1H-benzimidazol-2-one Form II.

Differential scanning calorimetry (DSC) analysis was performed on the crystal form II in Example 2. The DSC pattern of the crystal form II is shown in FIG. 5, wherein the first stage is a crystal form II crystal transformation process by heating, and the second stage is the melting process after the crystal transformation.

The thermogravimetric (TGA) analysis was carried out on the crystal form II in Example 2, using a TA Q500 thermogravimetric analyzer using a N2 atmosphere at a heating rate of 10° C./min.

Figure 8:
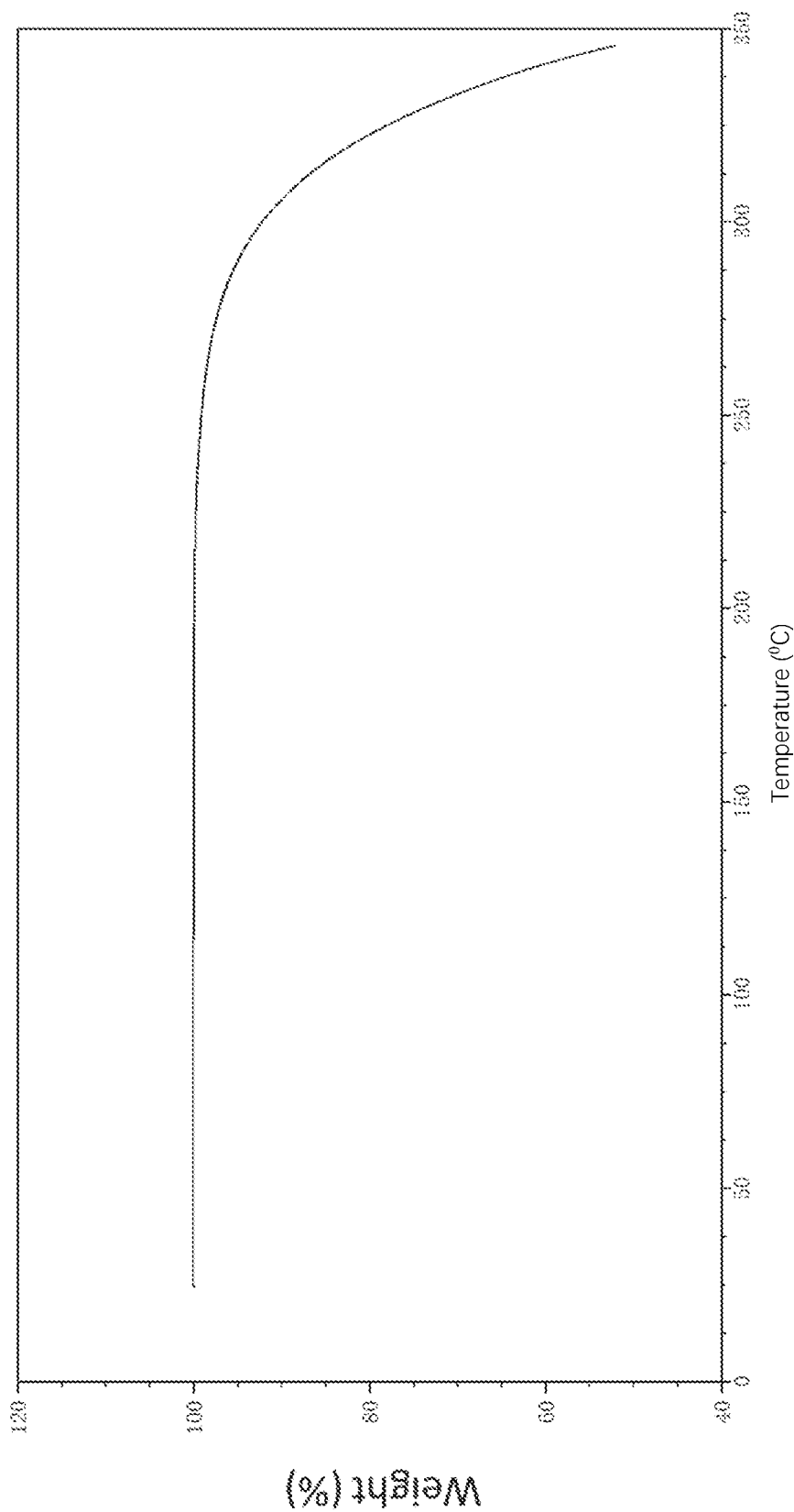
FIG. 8 TGA plot of [2-(4-(3-trifluoromethyl-benzyl)piperazin-1-yl)ethyl]-2,3-dihydro-1H-benzimidazol-2-one Form II.

The TGA plot of Form II is shown in FIG. 8. There is no obvious weight loss before 200° C.

Example 31

Dissolving 100 mg of [2-(4-(3-trifluoromethyl-benzyl)piperazin-1-yl)ethyl]-2,3-dihydro-1H-benzimidazol-2-one in 1 ml 2-methyltetrahydrofuran, this solution was added dropwise to 4 ml of 0° C. n-heptane, and the solid was precipitated and filtered to give [2-(4-(3-trifluoromethyl-benzyl)piperazin-1-yl)ethyl]-2,3-dihydro-1H-benzimidazol-2-one Form V.

Figure 3:
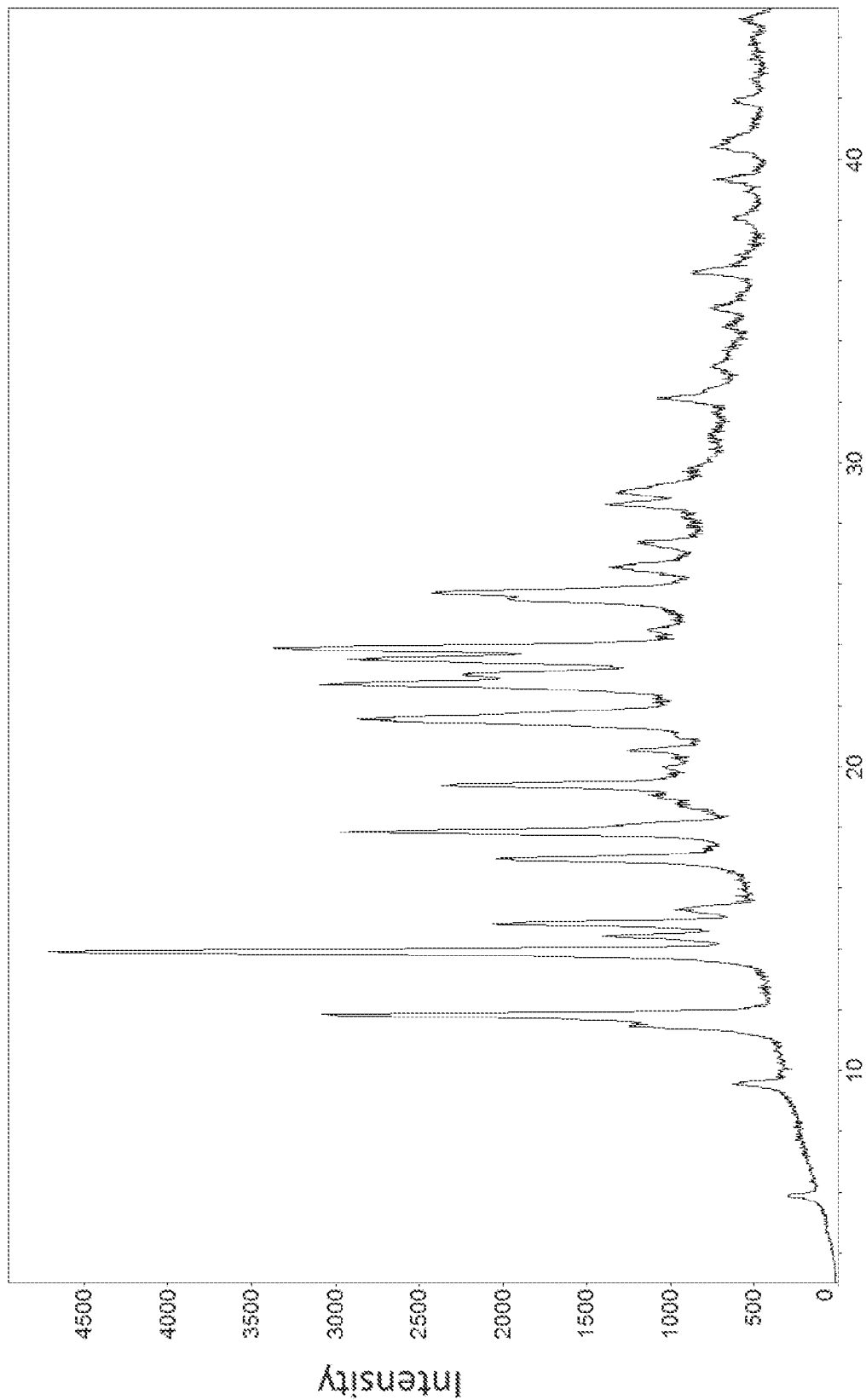
FIG. 3 XPRD pattern of [2-(4-(3-trifluoromethyl-benzyl)piperazin-1-yl)ethyl]-2,3-dihydro-1H-benzimidazol-2-one Form V.

[2-(4-(3-trifluoromethyl-benzyl)piperazin-1-yl)ethyl]-2,3-dihydro-1H-benzimidazol-2-one designated as Form I, has an X-ray powder diffraction pattern comprising the following 2θ values measured using CuKα radiation: 13.9±0.2, 11.9±0.2, 17.9±0.2, 23.9±0.2, 21.6±0.2, 22.7±0.2, 23.5±0.2, 19.4±0.2, 25.7±0.21, 4.8±0.2, 14.4±0.2, 17.0±0.2, 23.0±0.2, 11.5±0.2. The XRPD patterns is shown in FIG. 3 and the diffraction peaks of the XRPD pattern of Form V are listed in the following table:

| 2-Theta | d(A) | I(Height)% |
|---|---|---|
| 5.9 | 14.9674 | 5.7 |
| 9.579 | 9.2255 | 8.1 |
| 11.481 | 7.7013 | 21.5 |
| 11.858 | 7.4568 | 66.4 |
| 13.92 | 6.3566 | 100 |
| 14.439 | 6.1293 | 19 |
| 14.84 | 5.9645 | 34.9 |
| 15.302 | 5.7854 | 8.6 |
| 16.98 | 5.2175 | 34.1 |
| 17.861 | 4.962 | 55.8 |
| 19.382 | 4.5759 | 38.1 |
| 20.01 | 4.4337 | 2.5 |
| 20.542 | 4.3201 | 8.7 |
| 21.599 | 4.111 | 47 |
| 22.721 | 3.9105 | 46.7 |
| 23.021 | 3.8602 | 23.4 |
| 23.54 | 3.7761 | 41 |
| 23.919 | 3.7173 | 54.4 |
| 24.521 | 3.6272 | 3.5 |
| 25.52 | 3.4875 | 25.8 |
| 25.701 | 3.4634 | 37 |
| 26.58 | 3.3508 | 11.1 |
| 27.416 | 3.2504 | 7.7 |
| 28.64 | 3.1143 | 13.2 |
| 29.02 | 3.0743 | 12.4 |
| 32.122 | 2.7842 | 10.2 |
| 35.119 | 2.5531 | 5.4 |
| 36.261 | 2.4753 | 8.9 |
| 39.343 | 2.2882 | 6.9 |
| 40.4 | 2.2308 | 7.5 |
| 41.864 | 2.1561 | 3.8 |

Figure 6:
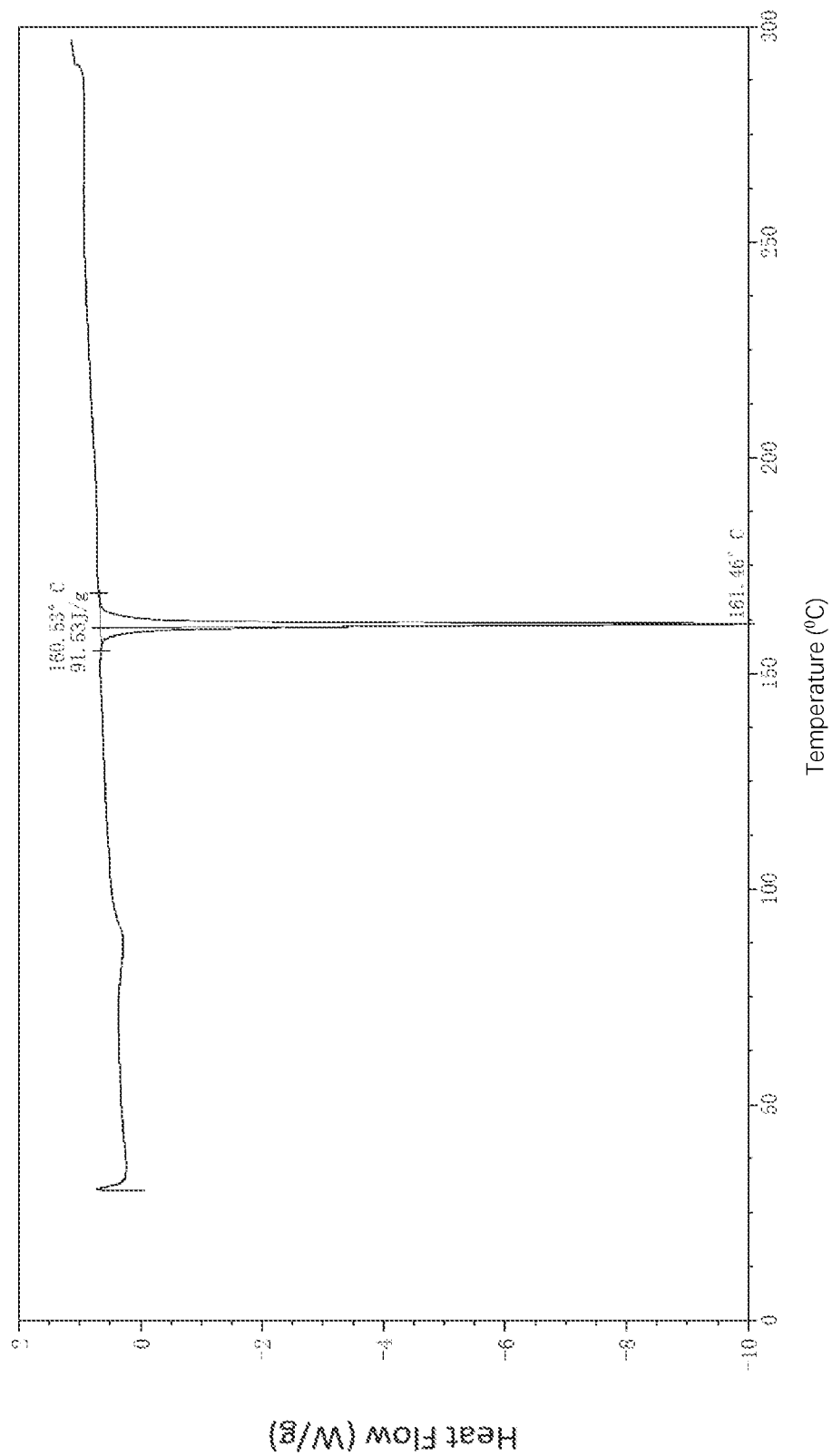
FIG. 6 DSC plot of [2-(4-(3-trifluoromethyl-benzyl)piperazin-1-yl)ethyl]-2,3-dihydro-1H-benzimidazol-2-one Form V.

The Form V in Example 31 was subjected to differential scanning calorimetry (DSC) analysis. The DSC plot of Form V is shown in FIG. 6, and a melting peak was obtained at about 161° C.

The crystal form V in Example 31 was subjected to thermogravimetric (TGA) analysis using a TA Q500 thermogravimetric analyzer using a N2 atmosphere at a heating rate of 10° C./min.

Figure 9:
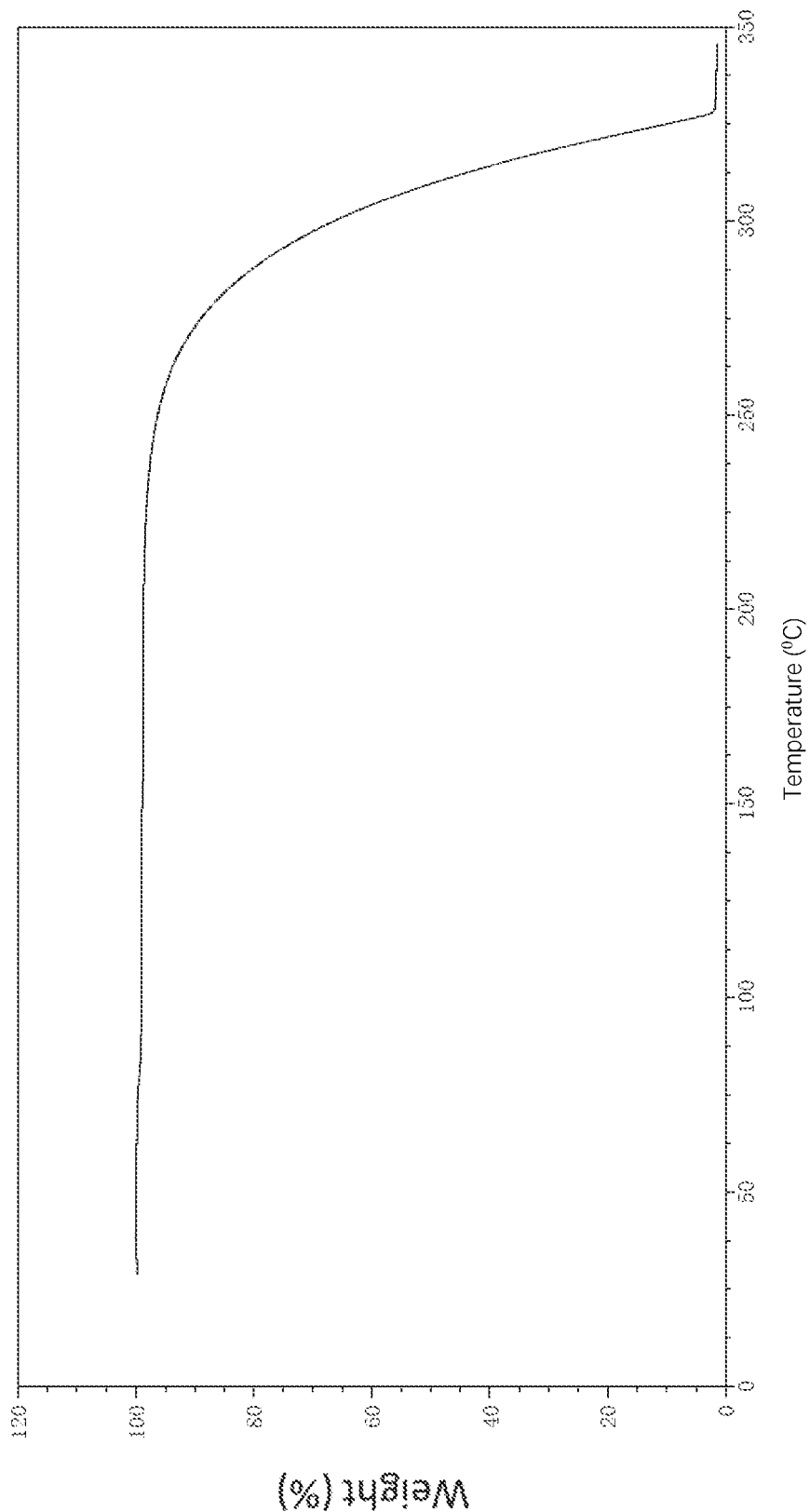
FIG. 9 TGA plot of [2-(4-(3-trifluoromethyl-benzyl)piperazin-1-yl)ethyl]-2,3-dihydro-1H-benzimidazol-2-one Form V.
Figure 10:
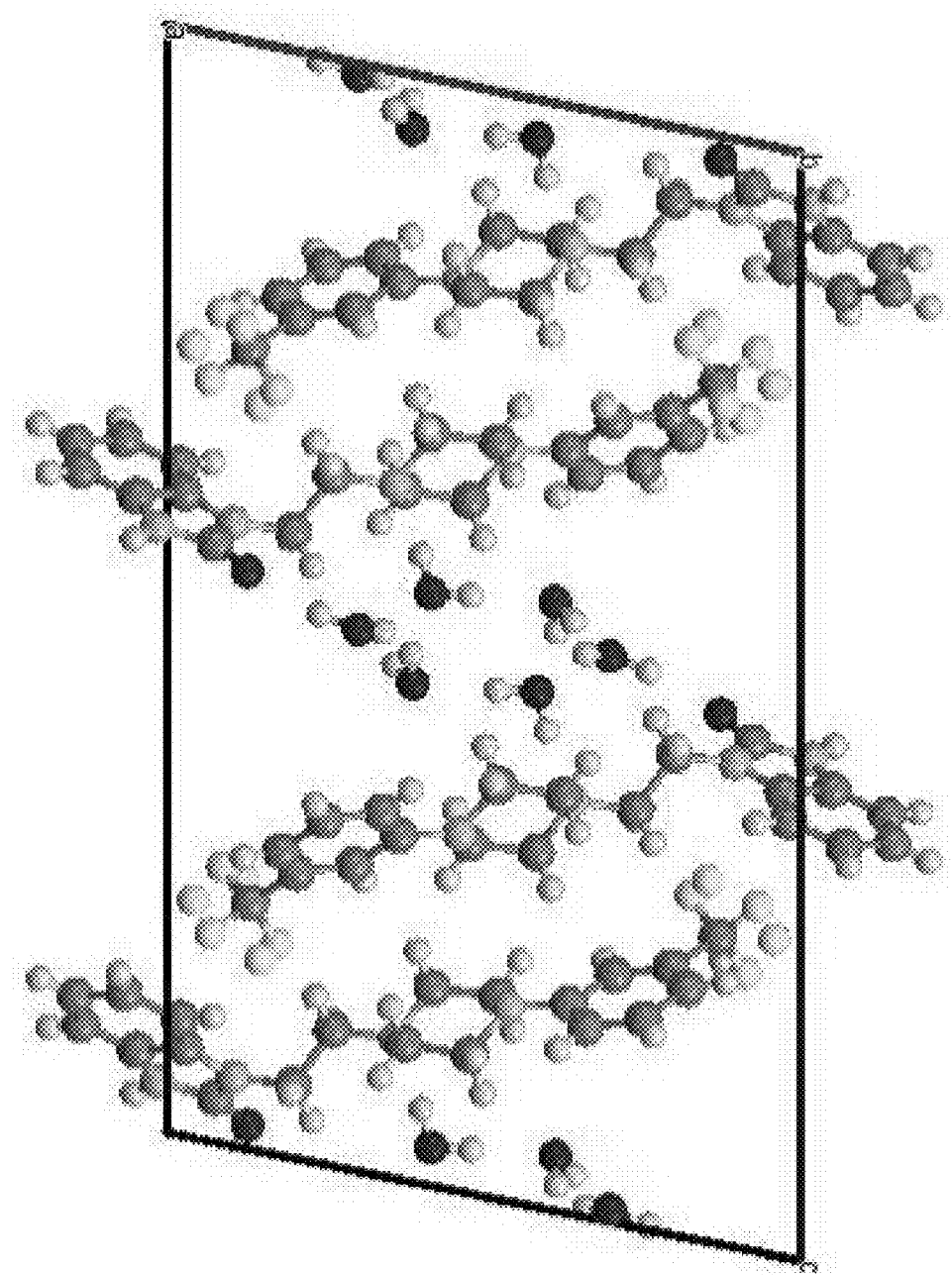
FIG. 10 Crystal structure of [2-(4-(3-trifluoromethyl-benzyl)piperazin-1-yl)ethyl]-2,3-dihydro-1H-benzimidazol-2-one Form I refined by single crystal X-ray diffraction.
Figure 11:
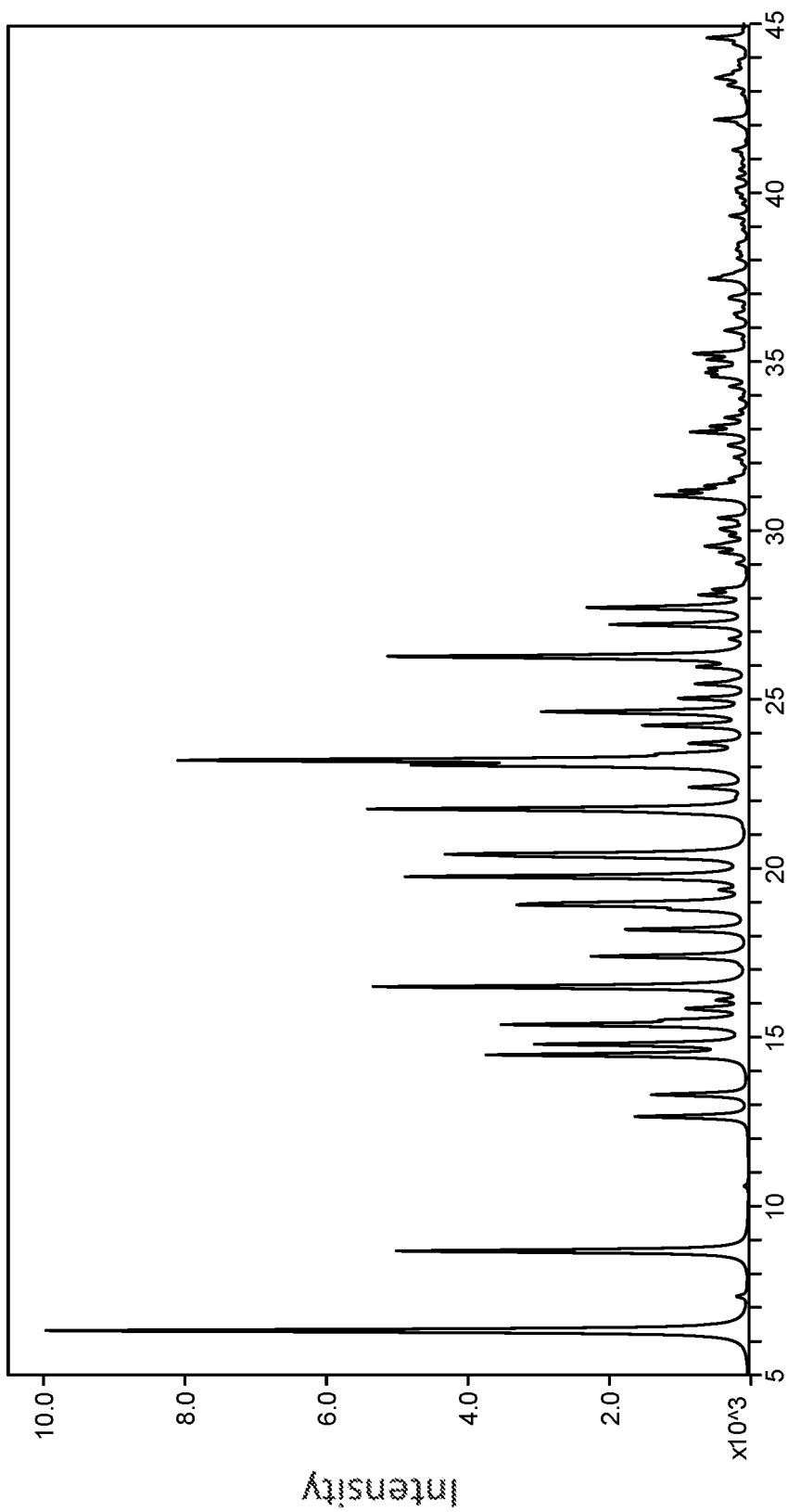
FIG. 11 standard XRPD pattern of [2-(4-(3-trifluoromethyl-benzyl)piperazin-1-yl)ethyl]-2,3-dihydro-1H-benzimidazol-2-one Form I (simulated by single crystal data).

The TGA plot of Form V is shown in FIG. 9, and there is no obvious weight loss before 200° C.

Example 32

The solubility of several new crystal forms prepared in the above examples and Form A (prepared according to the method of WO2003/014079) in a pH buffer solution (pH 6.8) was determined. Precisely weigh 20 mg Form I, Form II, Form V and Form A in a 2-mL glass vial, add 1 mL of pH 6.8 buffer, seal with cap, and mix on a rotating mixer. After the suspension was equilibrated for 1 hour, the mixture was filtered through a 0.45 μm needle filter, and the concentration of flibanserin in the filtrate was analyzed by HPLC to obtain the solubility of different crystal forms. The solubility of the polymorphs of Flibanserin is shown in the following table:

| Polymorphs | Form I | Form II | Form V | Form A |
|---|---|---|---|---|
| Solubility in pH 6.8 buffer (mg/mL) | 0.004 | 0.008 | 0.010 | 0.002 |

Example 33

Crystalline Form I single crystal culture process is described as following; weigh about 15 mg of flibanserin in 4-mL clean glass vial, then add 0.4 mL of n-propanol/water mixture solution (1:2, v/v). The mixture was dissolved by heating, filtered by a hot needle filter (tetrafluoroethylene membrane having a pore size of 0.2 μm), and then naturally cooled and then stored at 4° C. to precipitate a single crystal.

What is claimed is:
1. A crystalline form of [2-(4-(3-trifluoromethyl-benzyl)piperazin-1-yl)ethyl]-2,3-dihydro-1H-benzimidazol-2-one designated as Form V, having an X-ray powder diffraction pattern comprising the following 2θ values measured using CuKα radiation: 13.9±0.2, 11.9±0.2, 17.9±0.2, 23.9±0.2, and 21.6±0.2, wherein the X-ray powder diffraction pattern further comprises the following 2θ values measured using CuKα radiation: 22.7±0.2, 23.5±0.2, 19.4±0.2, 25.7±0.2, and 14.8±0.2 and the following 2θ values measured using CuKα radiation 14.4±0.2, 17.0±0.2, 23.0±0.2, and 11.5±0.2, 15.3±0.2, 20.0±0.2, 24.5±0.2, 40.4±0.2, and 41.9±0.2.

2. A pharmaceutical composition comprising the crystal in Form V according to claim 1 as an active ingredient.

3. A process for the preparation of [2-(4-(3-trifluoromethyl-benzyl)piperazin-1-yl)ethyl]-2,3-dihydro-1H-benzimidazol-2-one Form V according to claim 1 comprising:
   (i) dropwise adding a solution of 2-(4-(3-trifluoromethyl-phenyl)piperazin-1-yl)ethyl]-2,3-dihydro-1H-benzene imidazolidin-2-one in 2-methyltetrahydrofuran to a poor solvent to precipitate a solid; and
   (ii) obtaining crystal form V after filtration.

4. A method of treating or delaying hypoactive sexual desire disorder (HSDD) in premenopausal women, comprising administering to a subject in need thereof a pharmaceutical composition comprising crystalline [2-(4-(3-trifluoromethyl-benzyl)piperazin-1-Methyl]-2,3-dihydro-1H-benzimidazol-2-one in Form V of claim 1.

* * * * *